(12) United States Patent
Fantucci et al.

(10) Patent No.: US 6,211,380 B1
(45) Date of Patent: Apr. 3, 2001

(54) PROCESS FOR THE PREPARATION OF HETEROARYL-ZINC HALIDES

(75) Inventors: Mario Fantucci; Francesco Santangelo, both of Milan (IT)

(73) Assignee: Zambon Group S.p.A., Vicenza (IT)

( * ) Notice: Subject to any disclaimer, the term of this patent is extended or adjusted under 35 U.S.C. 154(b) by 0 days.

(21) Appl. No.: 09/341,297

(22) PCT Filed: Jan. 12, 1998

(86) PCT No.: PCT/EP98/00126

§ 371 Date: Jul. 8, 1989

§ 102(e) Date: Jul. 8, 1999

(87) PCT Pub. No.: WO98/31687

PCT Pub. Date: Jul. 23, 1998

(30) Foreign Application Priority Data

Jan. 17, 1997 (IT) .............................................. MI97A0081

(51) Int. Cl.[7] .............................. C07F 3/06; C07D 293/00
(52) U.S. Cl. ............................................. 548/101; 556/121
(58) Field of Search .............................. 556/121; 548/101

(56) References Cited

FOREIGN PATENT DOCUMENTS 9315086    5/1993   (WO) .

OTHER PUBLICATIONS

Xiaoming Wu et al., "Preparation of 3–Thienylzinc and magnesium Halide via Oxidative Addition of active Zinc and Magnesium to 3–Iodothiophene" *Chemical Abstracts*, vol. 124, No. 5, Jan. 29, 1996.

Tian An Chen et al., "The First Regioregular Head–to–tail Poly(3–hexylthiophene–2, 5–diyl) and a Regiorandom Isopolymer: Nickel versus Palladium Catalysis of 2(5)–bromo–5(2)–(bromozincio)–e–hexylthiop Hene Polymerization", *Chemical Abstracts*, vol. 117, No. 26, Dec. 28, 1992.

*Primary Examiner*—Porfirio Nazario-Gonzalez
(74) *Attorney, Agent, or Firm*—Arent, Fox, Kintner, Plotkin & Kahn

(57) ABSTRACT

A process for the preparation of heteroaryl-zinc halides of the formula (II): Het—Zn—X, wherein Het is an optionally substituted 5 or 6 membered aromatic heterocyclic group with one or two heteroatoms selected among nitrogen, oxygen or sulphur; X is a chlorine, bromine or iodine atom; comprising metallation reaction of heteroarylhalide with metallic zinc optionally activated by washing with acids, is described. Compounds of the formula (II) are intermediates useful in the synthesis for the preparation of compounds endowed with pharmacological activity.

13 Claims, No Drawings

PROCESS FOR THE PREPARATION OF HETEROARYL-ZINC HALIDES

The present invention relates to a process for the preparation of heteroaryl-zinc halides and, more particularly, it relates to a process for the preparation of heteroaryl-zinc halides by metallation reaction with metallic zinc.

The organo-zinc compounds are well-known compounds, extensively described in the literature.

More particularly, the heteroaryl-zinc halides such as, for example, 2-furyl, 2-thienyl, 2-pyridyl and 3-pyridyl-zinc chloride have been described by F. Tair Luo et al. in Heterocycles, Vol. 31, No. 12, 1990, 2181–2186.

Such compounds are used as synthetic intermediates for the preparation of many organic compounds, which are useful, for example, in the pharmaceutical and agrochemical field, in the polymer, dyestuff and synthetic fibres industries.

In the co-pending International patent application having the title "Process for the preparation of heteroaryl-phenylalanines" and claiming the Italian priority no. MI96A002738 of Dec. 24, 1996 in the name of the same Applicant, the heteroaryl-zinc halides are used as synthetic intermediates in the cross-coupling reaction for the preparation of heteroaryl-phenylalanines of formula

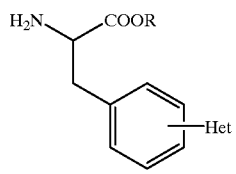
(I)

wherein
R is a hydrogen atom, a $C_1$–$C_4$ straight or branched alkyl group or a benzyl group;
Het is an optionally substituted 5 or 6 membered aromatic heterocyclic group having one or two heteroatoms selected among nitrogen, oxygen and sulphur.

In the literature a few synthetic processes for the preparation of organo-zinc compounds starting from metallic zinc are known.

In particular, as described by L. Zhu et al. in J. Org. Chem. 1991, 56, 1445–1453, some organo-zinc derivatives can be prepared by reaction of the corresponding halo-derivatives with metallic zinc, activated according to conventional procedures.

Substantially such methods of activation include the washing of zinc with aqueous diluted solutions of acids or bases or otherwise the use of particularly reactive alkyl halides able to initiate the metallation reaction such as, for example, 1,2-dibromoethane.

Nevertheless, as reported by the same Author, the use of activated zinc was useful just with respect to particularly reactive alkyl halides, for example alkyl iodides or α-halo-esters.

In the International patent application No. WO 93/15086 (Board of Regents of the University of Nebraska) a process for the preparation of organo-zinc derivatives such as for example, 2-bromo-5-bromozinc-thiophene (that is 5-bromo-2-thienyl-zinc bromide) is described.

More particularly, such a process comprises the reduction of suitable zinc (II) salts with alkaline or alkaline-earth metals, in a non hydroxylic solvent, for example an ether or an hydrocarbon, preferably in the presence of naphthalene derivatives and, subsequently, the reaction with suitable organic halo-derivatives.

Nevertheless, the above process is rather tedious and hard-working and not suitable for industrial application.

Moreover, the use of particularly reactive alkaline or alkaline-earth metals requires proper safety procedures.

In our knowledge, no processes for the preparation of hetero-zinc derivatives by metallation reaction with metallic zinc have never been described in the literature.

Now we have found a process for the preparation of heteroaryl-zinc halides starting from metallic zinc, easy to practice and particularly suitable for industrial application.

Therefore, object of the present invention is a process for the preparation of heteroaryl-zinc halides of formula

wherein
Het is an optionally substituted 5 or 6 membered aromatic heterocyclic group with one or two heteroatoms selected among nitrogen, oxygen or sulphur;
X is a chlorine, bromine or iodine atom;
that comprises the metallation reaction of a compound of formula

in which
Het and X have the above reported meanings;
characterised in that the metallation reaction is carried out with metallic zinc, optionally previuosly activated by washing with acids.

The process object of the present invention is easy to be industrially applied and it enables to obtain the compounds of formula II with high yields and with an elevated degree of purity.

The metallic zinc used in the process object of the present invention is powdered zinc The metallation reaction is carried out by using a molar ratio compound of formula III: zinc from 1:1 to 1:2.

Higher zinc amounts are likewise effective but useless.

Preferably a slight excess of zinc is used.

Zinc can be used as such or it can be useful to activate it if it is desired to increase its reactivity.

The optional activation of the metallic zinc is carried out by washing with acids. preferably by washing with diluted aqueous solutions of mineral acids.

More preferably, diluted aqueous solutions of mineral inorganic acids selected among sulfuric, hydrochloric, hydrobromic and hydroiodic acids are used.

For practical reasons, diluted aqueous solutions of hydrochloric acid are used.

Usually, the concentration of the acid in the aqueous solution is comprised between 0.1% and 10% by weight.

Preferably aqueous solutions containing from 0.5 to 3% of acid are used.

After the activation by washing with acids according to what above reported, the activated zinc will be further washed with water up to neutral pH, optionally with organic solvents too and then dried.

Therefore, the optionally activated metallic zinc is used, according to the present process, in the metallation reaction for the preparation of the compounds of formula II.

The metallation reaction according to the present invention is carried out in the presence of an organic solvent such as, for example, diethyl ether, methyl-tert-butyl ether, dioxane, ethylene glycol dimethyl ether, tetrahydrofuran, toluene, xylene or mixture thereof Preferably tetrahydrofuran, toluene or mixtures thereof are used.

The reaction temperature is comprised between 20° C. and the reflux temperature of the reaction mixture.

Preferably the reaction is carried out at reflux temperature.

Preferably, the preparation of the compounds of formula II, according to the present process, is carried out starting from a compound of formula III in which X is a bromine atom.

The starting compound of formula III are known compounds or easily obtainable according to known methods as described, for example, in J. Am. Chem. Soc. 1952, 74, 6260–6262.

Also the metallic zinc is an easily available commercial product.

From a practical point of view it is evident to the man skilled in the art that the compounds of formula II will not be isolated but directly used as intermediates in the same reaction medium.

Examples of compounds of formula II obtainable according to the process object of the present invention are the compounds in which the Het group is an aromatic heterocyclic group such as, for example, thiazole, isoxazole, oxazole, isothiazole, pyrazole, imidazole, thiophene, pyrrole, pyridine, pyrimidine, pyrazine, pyridazine and furan.

Preferred compounds of formula II are the compounds in which Het is thiophene or thiazole.

As previously disclosed, the compounds of formula II can be used as synthetic intermediates for the preparation of many organic compounds.

According to a particularly advantageous aspect of the process object of the present invention, the compounds of formula II, prepared as previously described, are directly used as synthetic intermediates in the same reaction medium, for example, for the preparation of the heteroaryl-phenylalanines of formula I as disclosed in the already cited co-pending International patent application.

Therefore, in a preferred practical embodiment thereof, the process object of the present invention is used for the preparation of heteroaryl-phenylalanines disclosed in the aforesaid International patent application.

In a preferred practical embodiment of the process object of the present invention, a compound of formula III is added to a suspension containing a slight excess of powdered metallic zinc in a suitable solvent and at a selected temperature, for example at the boiling temperature.

Then the reaction mixture was kept under stirring at the selected temperature until the starting compound disappears.

The resultant mixture, containing the compound of formula II, is then directly used for the preparation of various organic compounds, for example of the heteroaryl-phenylalanines of formula I, by working accordingly to what disclosed in the examples.

The process object of the present invention enables to obtain the heteroaryl-zinc derivatives of formula II with high yields and with such a degree of purity to allow them to be directly used in the subsequent preparations without any further purification steps.

Moreover, the use of particularly stable starting compounds, easily available and characterised by an high safety of use, make the process object of the present invention particularly suitable for the industrial application.

With the aim to illustrate the present invention the following examples are now furnished.

EXAMPLE 1

Preparation of 2-thiazolyl-zincbromide and cross-coupling with N-formyl4-iodo-L-phenylalanine methyl ester To a mixture of tetrahydrofuran (230 g), toluene (100 g) and zinc dust (type S from Pometon S.p.A.—36 g; 0.55 g/atoms), kept under reflux (73° C.), under stirring and under inert atmosphere, 2-bromothiazole (83 g; 0.5 moles) was added portionwise (10 portions) in 5 hours.

The reaction mixture was kept under reflux for 1 hour.

After cooling the reaction mixture at 50° C., N-formyl-4-iodo-L-phenylalanine methyl ester (122 g; 0.359 moles) and, after 5 minutes, palladium acetate (0.39 g; 1.75 mmoles) and triphenylphosphine (1.38 g; 5.25 mmoles) were added.

The reaction was exothermic and the mixture was kept at 50° C.–60° C. for 1 hour (TLC eluant hexane:ethyl acetate= 7:3) and was then cooled at 30° C.

By addition of celite (1 g) and Tonsil decolourizing earth (1 g), the mixture was filtered and washed with toluene (20 ml).

The resulting suspension was then added with water (300 ml) and 33% hydrochloric acid (108 g).

After separation of the phases, methylene chloride (160 g) and, dropwise, 28% aqueous ammonia (90 ml) up to pH 5.4–5.5 were added.

The separated organic phase was evaporated to residue under vacuum yielding N-formyl-4-(2-thiazolyl)-L-phenylalanine methyl ester [95.4 g; 91.6% yield with respect to the starting N-formyl-4-iodo-L-phenylalanine methyl ester].

EXAMPLE 2

Preparation of the activated metallic zinc

Powdered zinc (100 g) was added to an aqueous solution of 2% hydrochloric acid (250 ml) and the resulting suspension was kept under vigorous stirring for 5 minutes.

After settling of the suspension and removing of the supernatant, a 2% aqueous solution of hydrochloric acid (80 ml) was added again, keeping the suspension under vigorous stirring for 1 minute.

After settling and elimination of the supernatant the above procedure was repeated with additional parts of 2% hydrochloric acid (2×80 ml).

The final suspension was filtered under vacuum on a Bukner filter and repeatedly washed with water (3×80 ml) and with ethanol (3×80 ml).

Therefore the activated zinc, usable as such in the next preparations, was obtained (94 g) by drying under vacuum at 70° C.

EXAMPLE 3

Preparation of 2-thiazolyl-zincbromide and cross-coupling with N-(tert-butoxycarbonyl)4-iodo-L-phenylalanine methyl ester A solution of 98% 2-bromothiazole (2.07 ml; 23 mmoles) in tetrahydrofuran (10 ml) was slowly added, under nitrogen, to a suspension of activated metallic zinc (1.654 g; 25.3 mmoles), prepared as described in example 2, in tetrahydrofuran (10 ml).

The reaction mixture was kept under stirring at the boiling temperature for 1.5 hours (TLC eluant hexane:ethyl acetate= 9:1).

After cooling the reaction mixture at 40° C., N-(tert-butoxycarbonyl)-4-iodo-L-phenylalanine methyl ester (8.62 g; 20 mmoles), palladium acetate (0.067 g; 0.3 mmoles), triphenylphosphine (0.157 g; 0.6 mmoles) and toluene (20 ml) were orderly added.

The reaction mixture was kept under stirring at 50° C. for one hour (TLC eluant hexane:ethyl acetate=6:4) and was then cooled at room temperature.

By addition of celite (1 g) and Tonsil decolourizing earth (1 g), the mixture was filtered and washed with toluene (20 ml).

The resulting solution was then washed with water (15 ml) containing acetic acid (0.3 ml) and with water again (3×15 ml).

The separated organic phase was dried over sodium sulphate and the resulting solution was thus evaporated under vacuum yielding N-(tert-butoxycarbonyl)4-(2-thiazolyl)-L-phenylalanine methyl ester [8.9 g; 92% yield with respect to the starting N-(tert-butoxycarbonyl)4-iodo-L-phenylalanine methyl ester].

What is claimed is:

1. A process for the preparation of heteroaryl-zinc halides of the formula

Het—Zn—X (II)

wherein

Het is an optionally substituted 5 or 6 membered aromatic heterocyclic group with one or two heteroatoms selected from among nitrogen, oxygen or sulfur; and X is a chlorine, bromine or iodine atom;

that consists essentially of the metallation reaction of a compound of formula

Het—X (III)

in which

Het and X have the above reported meanings;

characterized by the fact that the metallation reaction is carried out with metallic zinc dust, optionally activated by washing with acids.

2. A process according to claim 1 in which the metallic zinc dust is activated by washing with diluted aqueous solutions of mineral acids.

3. A process according to claim 2 in which the mineral acids are selected among sulfuric, hydrochloric, hydrobromic and hydroiodic acids.

4. A process according to claim 3 in which the mineral acid is hydrochloric acid.

5. A process according to claim 2 in which the concentration of the acid in the aqueous solution is comprised between 0.1% and 10% by weight.

6. A process according to claim 5 in which the concentration of the acid is comprised between 0.5% and 3% by weight.

7. A process according to claim 1 in which the molar ratio compound of formula III: zinc is from 1:1 to 1:2.

8. A process according to claim 1 in which the metallation reaction is carried out in the presence of an organic solvent selected among diethyl ether, methyl-tert-butyl ether, dioxane, ethylene glycol dimethyl ether, tetrahydrofuran, toluene, xylene or mixture thereof.

9. A process according to claim 1 that comprises the metallation reaction of a compound of formula III in which X is a bromine atom.

10. A process according to claim 1 for the preparation of a compound of formula II in which Het is an aromatic heterocyclic group selected among thiazole, isoxazole, oxazole, isothiazole, pyrazole, imidazole, thiophene, pyrrole, pyridine, pyrimidine, pyrazine, pyridazine and furan.

11. A process according to claim 10 in which Het is thiophene or thiazole.

12. A process for preparing heteroaryl-phenylalanines of the formula I

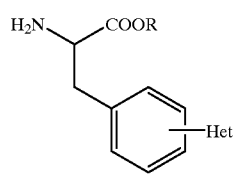

wherein

R is a hydrogen atom, a straight or branched C1–C4 alkyl group or benzyl group;

Het is an optionally substituted 5 or 6 membered aromatic heterocyclic group containing one or two heteroatoms selected from the group consisting of nitrogen, oxygen and sulphur;

said process comprising reacting a halo substituted compound of the formula III

Het—X III wherein

Het has the meaning above and X is selected from the group consisting of chlorine, bromine and iodine, with metallic zinc optionally activated with washing acids to generate Het—Zn—X and thereafter conducting a cross-coupling reaction to generate the compound of formula I.

13. The method of claim 12 wherein the zinc is zinc dust.

* * * * *